(12) United States Patent
Bishop et al.

(10) Patent No.: US 7,077,834 B2
(45) Date of Patent: Jul. 18, 2006

(54) PANT-LIKE DISPOSABLE GARMENT FOR ABSORBING HUMAN DISCHARGE

(75) Inventors: David Fleger Bishop, Appleton, WI (US); Bridget Ann Balogh, Menasha, WI (US); Mary Jo Meyer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 525 days.

(21) Appl. No.: 10/394,358

(22) Filed: Mar. 21, 2003

(65) Prior Publication Data

US 2004/0186451 A1 Sep. 23, 2004

(51) Int. Cl.
*A61F 13/20* (2006.01)

(52) U.S. Cl. ............... 604/385.11; 604/385.01; 604/387; 604/389; 604/391; 604/394

(58) Field of Classification Search ............ 604/385.03, 604/385.11, 386, 389, 391, 395, 396
See application file for complete search history.

(56) References Cited

U.S. PATENT DOCUMENTS

| | | | |
|---|---|---|---|
| 1,467,481 A | 1/1923 | Juline | |
| 1,695,109 A | 12/1928 | Kosloff | |
| 2,055,973 A | 9/1936 | Goss | |
| 2,102,359 A | 12/1937 | Frieman | |
| 2,278,029 A | 3/1942 | Walsh et al. | |
| 2,322,170 A | 6/1943 | Snyder | |
| 2,834,347 A | 5/1958 | Connally | |
| 3,008,366 A | 11/1961 | Taylor Jr. | |
| 3,056,323 A | 10/1962 | Kwitek | |
| 3,075,684 A | 1/1963 | Rothmann | |
| 3,561,332 A | 2/1971 | Ross | |
| 3,570,337 A | 3/1971 | Morgan | |

(Continued)

FOREIGN PATENT DOCUMENTS

| | | |
|---|---|---|
| DE | 197 46 456 A1 | 4/1999 |
| EP | 0 820 843 B1 | 1/2003 |
| GB | 2 267 024 A | 11/1993 |
| WO | WO 97/23398 A1 | 7/1997 |
| WO | WO 02/069867 A1 | 9/2002 |
| WO | WO 03/024372 A2 | 3/2003 |
| WO | WO 03/028604 A1 | 4/2003 |

*Primary Examiner*—Larry I. Schwartz
*Assistant Examiner*—Melanie J. Hand
(74) *Attorney, Agent, or Firm*—Thomas J. Connelly

(57) ABSTRACT

A pant-like disposable garment for absorbing human discharge is disclosed. The pant-like garment includes a front panel, a back panel, and an absorbent assembly. The absorbent assembly includes a bodyside liner, an outer cover, and an absorbent positioned therebetween. The absorbent assembly further including a pair of end edges and is secured to the front panel and to the back panel. The front and back panels are joined together by a pair of seams to form a waist opening and a pair of leg openings. The garment also includes a pair of perforation lines formed in the front panel with each being aligned non-parallel to one of the seams. The garment further includes a pair of attachment members which overlap the pair of perforation lines. The pair of perforation lines and the pair of attachment members function to allow the waist opening to be easily opened and closed more than once.

20 Claims, 3 Drawing Sheets

U.S. PATENT DOCUMENTS

| | | | |
|---|---|---|---|
| 3,762,542 A | 10/1973 | Grimes | |
| 3,800,796 A | 4/1974 | Jacob | |
| 3,823,623 A | 7/1974 | Currie et al. | |
| 3,826,165 A | 7/1974 | Currie et al. | |
| 3,860,003 A | 1/1975 | Buell | |
| RE28,911 E | 7/1976 | Jespersen et al. | |
| 4,205,679 A | 6/1980 | Repke et al. | |
| 4,610,189 A | 9/1986 | Lombardo | |
| 4,610,680 A | 9/1986 | LaFleur | |
| 4,639,949 A | 2/1987 | Ales et al. | |
| 4,745,835 A | 5/1988 | Schnitzer | |
| 4,769,023 A | 9/1988 | Goebel et al. | |
| 4,850,988 A | 7/1989 | Aledo et al. | |
| 4,850,992 A | 7/1989 | Amaral et al. | |
| 4,940,464 A | 7/1990 | Van Gompel et al. | |
| 5,074,854 A | 12/1991 | Davis | |
| 5,137,525 A * | 8/1992 | Glassman | 604/385.11 |
| 5,215,275 A | 6/1993 | Gold | |
| 5,236,430 A | 8/1993 | Bridges | |
| 5,246,433 A | 9/1993 | Hasse et al. | |
| 5,370,634 A | 12/1994 | Ando et al. | |
| 5,624,420 A * | 4/1997 | Bridges et al. | 604/365 |
| 5,836,228 A | 11/1998 | Guthrie et al. | |
| 6,036,805 A | 3/2000 | McNichols | |
| 6,401,586 B1 | 6/2002 | Wood | |
| 6,524,293 B1 | 2/2003 | Elsberg et al. | |
| 6,752,796 B1 | 6/2004 | Karami | |
| 6,849,067 B1 * | 2/2005 | Fletcher et al. | 604/389 |
| 2002/0045879 A1 | 4/2002 | Karami | |
| 2002/0148557 A1 | 10/2002 | Heller et al. | |
| 2003/0000357 A1 | 1/2003 | Tanaka | |
| 2003/0055389 A1 * | 3/2003 | Sanders et al. | 604/358 |
| 2003/0135192 A1 * | 7/2003 | Guralski et al. | 604/391 |

\* cited by examiner

PANT-LIKE DISPOSABLE GARMENT FOR ABSORBING HUMAN DISCHARGE

BACKGROUND OF THE INVENTION

Pant-like disposable garments for absorbing human discharges can appear similar in size and shape to regular cloth underwear which is designed to be laundered and reused two or more times. A disposable garment is an article intended to be worn by persons, including infants, toddlers, or adults, that is designed for single use or temporary use and is meant to be disposed of after being used once instead of being laundered or dry cleaned for re-use. Some examples of disposable garments include infant diapers, training pants, adult incontinence garments, feminine pants, etc.

Some pant-like disposable garments manufactured today resemble regular cloth underwear in that they have a waist opening and a pair of leg openings. Such pant-like disposable garments can be pulled up around the torso of a user in a similar fashion as regular cloth underwear. Still other pant-like disposable garments contain an attachment mechanism that will allow the garment to be opened into a flat configuration prior to being placed around the torso of a user. This design is beneficial for bed bound users who may be immobile and who need assistance in securing the garment in place. Still other pant-like garments contain attachment means for opening and closing the waist opening after the garment has been positioned around the torso of a user. This feature is advantageous in that the user does not have to undress when there is a desire to check the status of the absorbent garment. One pant-like disposable garment currently being commercially sold by Kimberly-Clark Corporation uses a pair of perforation lines with each extending from the waist opening to one of the leg openings. The perforation lines are designed to be broken either prior to positioning the garment around the user's torso or while the garment is already positioned about the user's torso. A pair of attachment members is then utilized to refasten the garment so that it is snug about the user's torso. This present design suffers from two deficiencies. Namely, a majority of each of perforation lines is visually hidden by the attachment members and some users cannot see them and thereby not know that they are present. Second, each perforation line may be ergonomically hard to tear open by older adults, some of who may be suffering from arthritis, because the perforation lines are aligned adjacent and parallel to the side seams.

Now a pant-like disposable garment for absorbing human discharge has been invented that uses a pair of perforation lines that are aligned non-parallel to the side seams to make them more visually noticeable and to enable the user to easily grasp the waist band on either side of the perforation lines and tear open the perforations. The pant-like disposable garment also possesses an aesthetically pleasing design with improved fit around the human torso.

SUMMARY OF THE INVENTION

Briefly, this invention relates to a pant-like disposable garment for absorbing human discharge. The pant-like disposable garment includes a front panel, a back panel, and an absorbent assembly. The absorbent assembly includes a liquid pervious bodyside liner, a liquid-impervious outer cover, and an absorbent positioned therebetween. The absorbent assembly further includes a pair of end edges and is secured to the front panel approximate one of the pair of end edges and is secured to the back panel approximate the other one of the pair of end edges. The front and back panels are joined together by a pair of seams to form a waist opening and a pair of leg openings. The garment also includes a pair of perforation lines formed in the front panel with each being aligned non-parallel to one of the seams. Each of the pair of perforation lines extends from the waist opening to one of the respective leg openings. The garment further includes a pair of attachments members, each having a first region and a second region. The first region of each attachment member is secured to one side of a perforation line and the second region extends forward over a portion of the respective perforation line and is removeably attached to the front panel. The pair of perforation lines and the pair of attachment members function to allow the waist opening to be easily opened and closed more than once.

DETAILED DESCRIPTION

Figure 1:
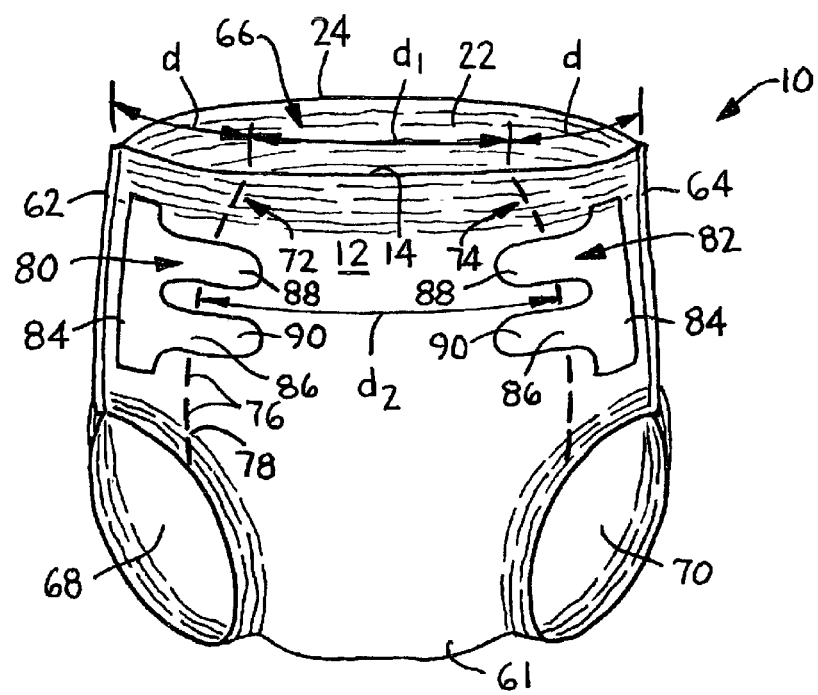
FIG. 1 is a perspective view of a pant-like disposable garment for absorbing human discharge that includes a pair of tearable perforation lines aligned non-parallel to a pair of side seams and further includes a pair of attachment members which bridge over a portion of the perforation lines.
Figure 2:
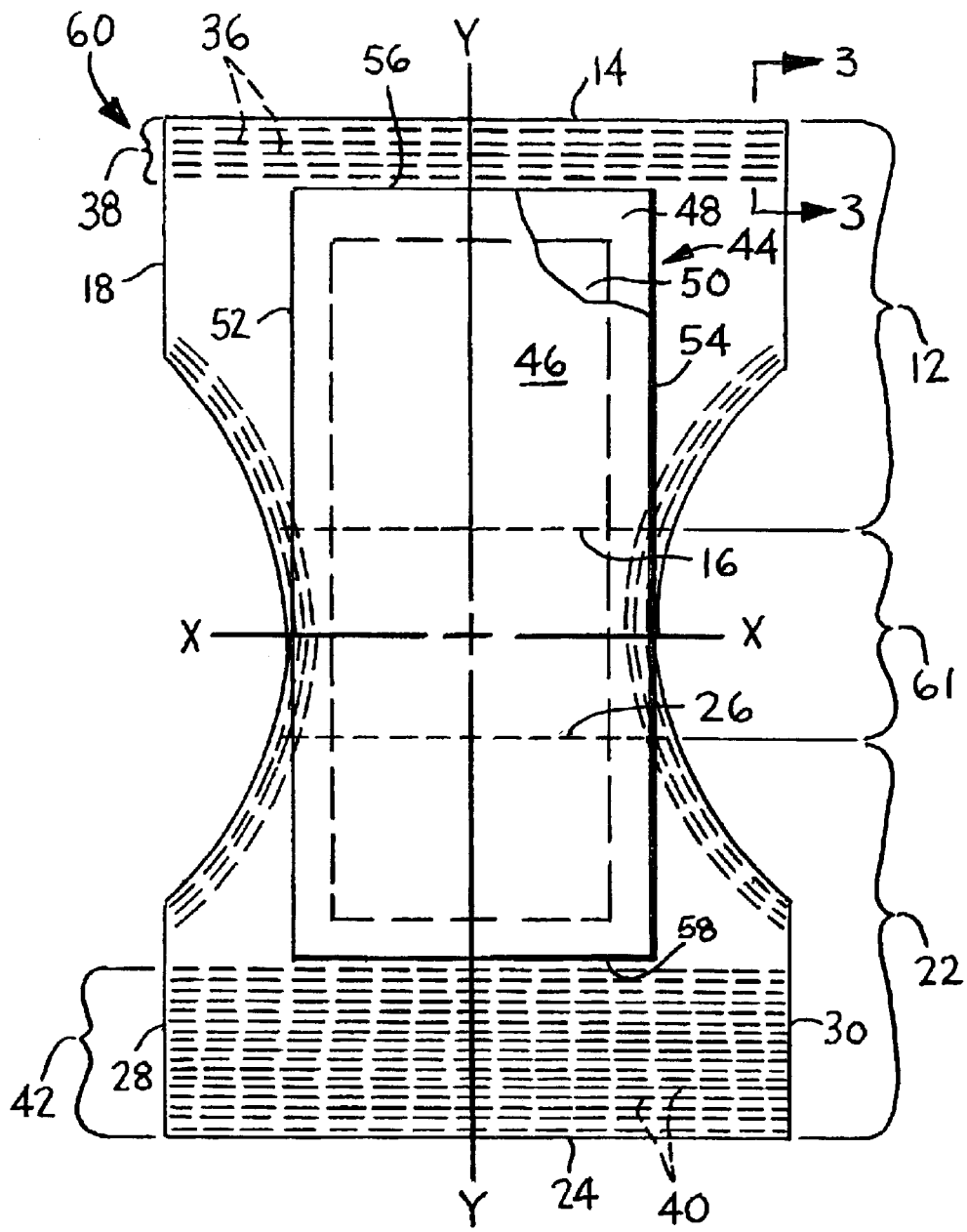
FIG. 2 is a plane view of a pant-like disposable garment before the front panel is secured to the back panel and showing the absorbent assembly secured to the front and back panels.

Referring to FIGS. 1 and 2, a pant-like disposable garment 10 for absorbing human discharge is shown. A "disposable garment" as used herein is an article that is intended to be worn by persons, including infants, toddlers or adults, which is designed for single use or temporary use and is meant to be disposed of after being used once instead of being laundered or dry cleaned for re-use. The pant-like disposable garment 10 is designed to absorb and/or retain one or more bodily discharges of waste material such as urine, perspiration, excrement, feces, menses, menstrual fluid, as well as other liquid and/or solid waste.

Figure 3:
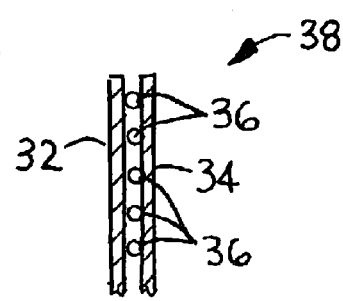
FIG. 3 is a cross-sectional view of FIG. 2 taken along line 3—3 showing a laminate structure with elastic strands sandwiched therebetween.

Referring to FIG. 2, the pant-like disposable garment 10 includes a front panel 12 having a first end 14, a second end 16, a first side 18, and a second side 20 and a back panel 22 having a first end 24, a second end 26, a first side 28, and a second side 30. The front and/or back panels, 12 and 22 respectively, can be formed from a single piece of material or they can be a laminate of two or more layers. The layers of the laminate can be of the same material or different material. In the cross-sectional view shown in FIG. 3, the front panel 12 is depicted as being formed from a first layer 32 and a second layer 34. Sandwiched between the first and second layers, 32 and 34 respectively, are two or more strands of elastic 36. Desirably, two to ten strands of elastic 36 are utilized in the front panel 12 to form a front waist band 38. The elastic strands 36 can be formed from LYCRA®. LYCRA® is a registered trademark of E. I. Du Pont De Nemours & Co., having an office at 1007 Market Street, Wilmington, Del. 19898. The diameter and/or cross-sectional configuration of the elastic strands 36, the decitex (weight in grams per 10,000 meters of a strand) of the elastic strands 36, and tension imparted into the elastic strands 36 can all be varied to suit one's particular product needs. The back panel 22 normally contains more elastic strands than the front panel 12 to assure that the pant-like garment 10 stays snug around the torso of the wearer. In FIG. 2, the back panel 22 is shown having from between about ten to about thirty strands of elastic 40 which form a back waist band 42. The elastic strands 40 can be formed from LYCRA® as well.

The front and/or back panels, 12 and 22 respectively, can be formed from a breathable or a non-breathable material. A polyolefin, such as polypropylene or polyethylene can be used as well as spunbond or a bonded carded web. A metallocene polypropylene works very well since it has a soft feel and can be easily ultrasonically bonded to itself.

The pant-like disposable garment 10 also includes an absorbent assembly 44. The absorbent assembly 44 includes a liquid pervious bodyside liner 46, a liquid-impervious outer cover 48, and an absorbent 50 positioned therebetween. The liquid pervious bodyside liner 46 is located nearest to the human body, adjacent to the skin of the user, and can be formed from a woven or non-woven material that will readily allow liquid or fluids to pass therethrough. The bodyside liner 46 is normally a very thin web that can be formed from natural or synthetic fibers, with or without apertures formed therein. A spunbond and a bonded carded web are two materials that work well as a bodyside liner 46. "Spunbond" is manufactured and sold commercially by Kimberly-Clark Corporation having an office at 401 North Lake Street, Neenah, Wis. 54956. The liquid-impervious outer cover 48 is located on the exterior of the disposable garment 10, away from the skin of the user. The liquid-impervious outer cover 48 is formed from a material which will restrict fluid from penetrating or passing therethrough so as to prevent the outer clothing of the wearer from becoming soiled. Desirably, the outer cover 48 has a soft feel so as not to chafe the inner thighs of the wearer. The outer cover 48 can also be formed from natural or synthetic fibers. The outer cover 48 can be formed from a material that is not noisy when squeezed or wrinkled so that the disposable garment 10 remains discreet. The outer cover 48 can also be formed from a breathable material. The outer cover 48 can further be formed from a laminate where one layer of the laminate is liquid-impervious. Examples of various materials that can be used as the outer cover 48 include a polyolefin, such as polypropylene or polyethylene; a liquid impervious layer bonded to a spunbond; and a thermoplastic material bonded to a spunbond. Other materials known to those skilled in the art can also be utilized.

The absorbent 50 is sealed within the liquid pervious bodyside liner 46 and the liquid-impervious outer cover 48. The absorbent 50 can be formed from natural or synthetic materials. The absorbent 50 can be made from cellulosic fibers, wood pulp, textile fibers or other absorbent materials known to those skilled in the art. Superabsorbents, in solid form and in the shape of small particles, granules, flakes, etc., can be mixed in with the absorbent material to increase the absorbent capacity of the absorbent 50.

The absorbent assembly 44 further includes a pair of side edges 52 and 54 and a pair of end edges 56 and 58. The absorbent assembly 44 is secured to the front panel 12 approximate the end edge 56 and is secured to the back panel 22 approximate the end edge 58. The absorbent assembly 44 can be secured to the front and back panels, 12 and 22 respectively, in a permanent fashion or in a removable fashion to enable a replacement assembly to be later substituted. The pair of end edges 46 and 58 can be secured to the front and back panels, 12 and 22 respectively, by any means known to those skilled in the art. Some examples of securement include the use of an adhesive, co-adhesives, glue, ultrasonics, stitching using thread, heat and/or pressure seals, mechanical means, etc. The exact distance the end edges 56 and 58 are spaced from the first ends, 14 and 24 respectively, of the front and back panels 12 and 22 can vary to optimize the functionality of the disposable garment 10. It should be noted that the distance the end edge 56 is spaced away from the first end 14 of the front panel 12 can be less than, equal to or greater than the distance that the end edge 58 is spaced away from the first end 24 of the back panel 22. For active adults, the absorbent assembly 44 may be positioned such that the end edges 56 and 58 are equally spaced from the first ends 14 and 24 of the front and back panels, 12 and 22 respectively. For a bedridden person, the absorbent assembly 44 can be positioned closer to the first end 24 of the back panel 22 so as to provide added protection against leakage of body fluid from a person lying in a recumbent manner. Desirably, for active adults wearing the disposable garment 10, the distance the end edge 56 of the absorbent assembly 44 is spaced away from the first end 14 of the front panel 12 is less than the distance that the end edge 58 of the absorbent assembly 44 is spaced away from the first end 24 of the back panel 22. This arrangement allows the absorbent assembly 44 to be skewed more towards the front of the pant-like garment 10 and function better for both male and female users.

When the front panel 12, the back panel 22 and the absorbent assembly 44 are secured together, a chassis 60 is formed having a central transverse axis X—X and a central longitudinal axis Y—Y. A crotch panel 61 is located between the front panel 12 and the back panel 22. This chassis 60 can be folded along the transverse axis X—X such that the first and second sides, 18 and 20 respectively, of the front panel 12 are aligned approximate with the first and second sides, 28 and 30 respectively, of the back panel 22.

Referring again to FIG. 1, the front and back panels, 12 and 22 respectively, are folded and joined together by a pair of seams 62 and 64 to form a waist opening 66 and a pair of leg openings 68 and 70. The seams 62 and 64 can be aligned parallel to one another or they can be angled relative to one another. Desirably, the seams 62 and 64 are aligned parallel to one another and are aligned parallel to the longitudinal axis Y—Y of the chassis 60. In this pant-like disposable garment 10, portions of the side edges 52 and 54 of the absorbent assembly 44 are aligned adjacent to the leg openings, 68 and 70 respectively, and portions of the end edges 56 and 58 of the absorbent assembly 44 are aligned adjacent to the waist opening 66.

Still referring to FIG. 1, the pant-like disposable garment 10 also includes a pair of perforation lines 72 and 74 formed in the front panel 12. Each perforation line 72 and 74 is aligned non-parallel to one of the seams 62 and 64. This unique configuration makes for a more aesthetically pleasing garment and one that is ergonomically easier to open. Each of the perforation lines 72 and 74 extends from the waist opening 66 to one of the respective leg openings 68 and 70. In addition, each of the perforation lines 72 and 74 are tearable by applying a minimum amount of pressure to the front waist band 38 on either side of the perforation lines 72 and 74. For example, the user can position his or her thumbs on the inside of the front waist band 38 and his or her index fingers on the outside of the front waist band 38. One hand will be positioned on one side of a perforation line 72 or 74 and the other hand will be positioned on the opposite side of the perforation line 72 or 74. The user can then simply apply pressure by moving his or her hands apart thereby creating tension across one of the perforation lines 72 or 74 which will cause it to tear apart.

Each of the perforation lines 72 and 74 consist of multiple land areas 76 aligned adjacent to open areas 78. The length of each of the land areas 76 can be less than, equal to, or be greater than the length of each of the open areas 78. The ratio between the length of a land to an open area, 76 and 78 respectively, can be adjusted to increase or decrease the amount of force required to break the pair of perforation lines 72 and 74. The type of material into which the perforation lines 72 and 74 are formed, the thickness of the material, the configuration of the perforation lines 72 and 74, as well as other features, will all have an impact on the amount of force needed to break the perforation lines 72 and 74. It should also be noted that the amount of force needed to start to break the perforation lines 72 and 74 may be slightly greater than the amount of force needed to continue to tear open the perforation lines 72 and 74.

The perforation lines 72 and 74 can be formed such that each of the land areas 76 has a length that is equal to the length of each of the open areas 78. Alternatively, the length of the land and/or open areas, 76 and 78 respectively, can vary along a portion of or over the total length of the perforation lines 72 and 74. It has been found that when the length of the open areas 78 is greater than the length of the land areas 76, that the perforation lines 72 and 74 can be easily broken. It is important to design the land and open areas, 76 and 78 respectively, such that the perforation lines 72 and 74 are easy for the user to break yet ensure that the perforation lines 72 and 74 will not break prematurely. Good results have been obtained by dimensioning the length of each of the open areas 78 to be at least two times greater than the length of each of the land areas 76. Desirably, the length of each of the open areas 78 will be at least three times greater than the length of each of the land areas 76. More desirably, the length of each of the open areas 78 will be at least four times greater than the length of each of the land areas 76.

Figure 6:
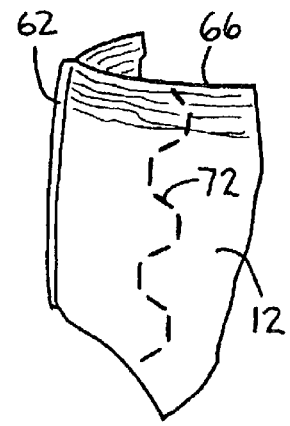
FIG. 6 is a front view of still another configuration of a perforation line arranged in a non-parallel relationship to the side seam.
Figure 7:
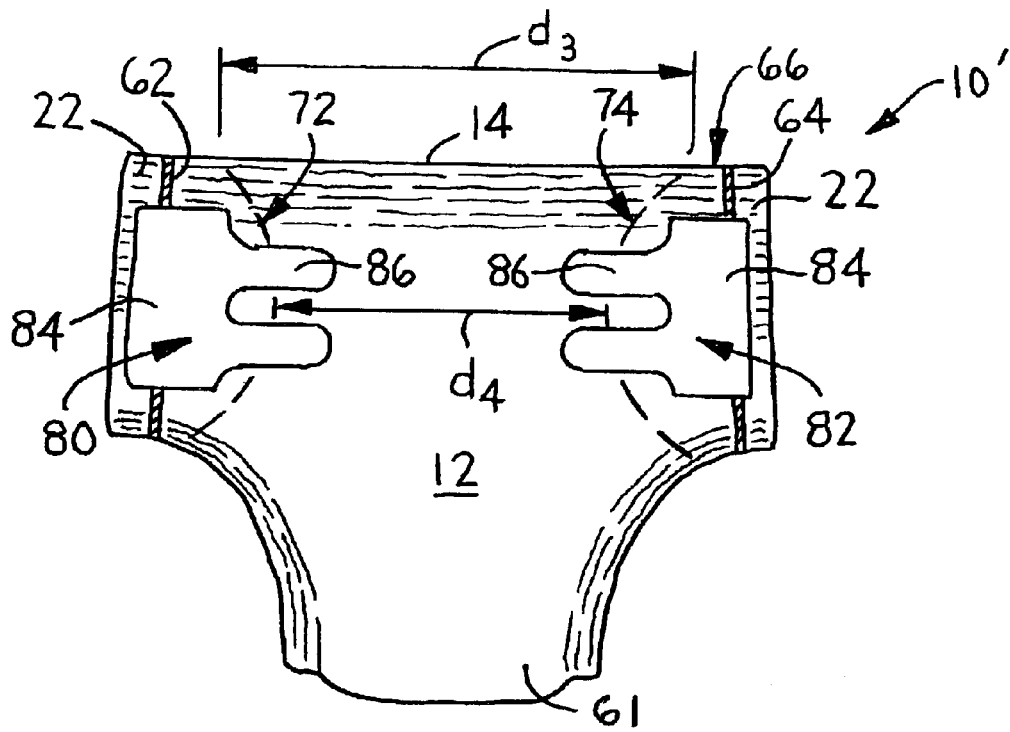
FIG. 7 is a plane view of a pant-like disposable garment showing a pair of attachment members each secured to the back panel and each extending forward over the side seam, as well as over a portion of the curved perforation line.

Referring again to FIGS. 1 and 4–8, each of the perforation lines, 72 and 74 respectively, is shown being aligned non-parallel to one of the seams, 62 and 64 respectively. As depicted in FIGS. 1 and 7, the perforation lines 72 and 74 also have a non-linear configuration. More particularly, in FIG. 1, the perforation lines 72 and 74 are curved or arcuate in shape and are arranged convex to the seams 62 and 64, respectively. The radius of a curved or arcuately shaped perforation line can vary. The exact radius will be partly dictated by the distance between the waist opening 66 and the respective leg opening 68 or 70. In FIG. 7, the perforation lines 72 and 74 are curved and are arranged convex to the seams, 62 and 64 respectively. By convex is meant a perforation line that curves or bulges outward, as the exterior of a sphere, away from the adjacent seam 62 or 64. It should be noted that the perforation lines 72 and 74 could be concave relative to one of the adjacent seams, 62 or 64 respectively. As shown in FIGS. 1 and 7, the perforation lines 72 and 74 form mirror images on one another if the disposable garment 10 or 10' was vertically divided along the longitudinal center line.

Figure 4:
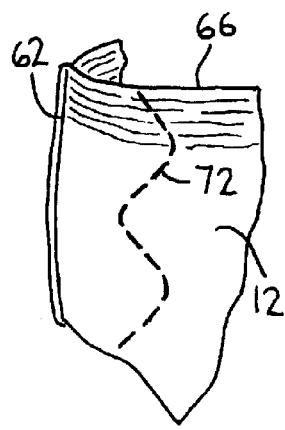
FIG. 4 is a front view of an alternative configuration of a perforation line arranged in a non-parallel relationship to the side seam.
Figure 5:
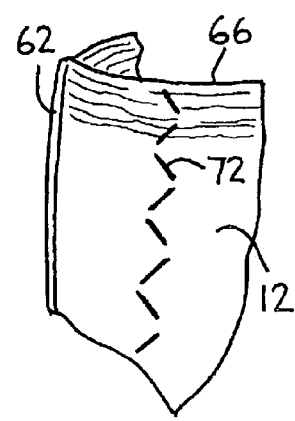
FIG. 5 is a front view of still another configuration of a perforation line arranged in a non-parallel relationship to the side seam.

The shape of the perforation lines 72 and 74 can vary and can be essentially almost any configuration. In FIG. 4, the perforation line 72 is shown having a sinusoidal configuration. The number of lobes in the sinusoidal pattern can vary to suit one's particular needs. In FIG. 5, the perforation line 72 is shown having a herringbone configuration. The herringbone configuration is a pattern of oblique parallel lines arranged as single lines alternating in direction. In FIG. 6, the perforation line 72 is shown having a saw toothed configuration where the lines are arranged in a serrated fashion. Lastly, in FIG. 8, each of the perforation lines 72 and 74 are linear lines arranged at an angle to one of the seams, 62 and 64 respectively. These as well as other shapes can be utilized in forming the perforation lines 72 and 74.

Each of the perforation lines 72 and 74 extend downward from the waist opening 66 to one of the respective leg openings 68 and 70. The exact position where the perforation lines 72 and 74 intersect the waist opening 66 and/or the respective leg openings 68 and 70 can vary. However, a sufficient distance (d) should be present between the points where the seam 62 and the perforation line 72 intersect the waist opening 66, and between the points where the seam 64 and the perforation line 74 intersect the waist opening 66. When the distance (d) is of a sufficient length, it will ensure that the user of the garment 10 can insert his or her thumbs and fingers onto the front waist band 38, on opposite sides of the perforation lines 72 and 74, and exert a force adequate to break the perforations. Desirably, the distance (d) should be at least about 1 inch (about 2.54 cm), more desirably, the distance (d) should be at least about 2 inches (about 5 cm), and most desirably, the distance (d) should be at least about 3 inches (about 7.5 cm). The exact dimension for the distance (d) will vary depending on the size and shape of the disposable garment 10.

Still referring to FIG. 1, one will notice that the pair of perforation lines 72 and 74 is separated by a distance $(d_1)$ adjacent to the waist opening 66. The pair of perforation lines 72 and 74 is also separated by a distance $(d_2)$ at a point located between the waist opening 66 and the pair of leg openings 68 and 70. The distance $(d_1)$ can be less than or greater than the distance $(d_2)$. When the distance $(d_1)$ is less than the distance $(d_2)$, it will assure that each of the perforation lines 72 and 74 are aligned in a non-parallel relationship to one of the seams, 62 and 64 respectively, as well as providing sufficient space at the waist opening 66 for the user to grasp the front waist band 38 and easily tear the perforations.

The pant-like disposable garment 10 further includes a pair of attachment members 80 and 82 each having a first region 84 and a second region 86. In FIG. 1, each of the first regions 84 is secured to the front panel 12 on one side of each of the perforation lines 72 and 74. The first regions 84 can be permanently attached to the front panel 12. By "permanently attached" is meant that the first regions 84 are secured to the front panel 12 and are not designed to be removable without destroying the bond or attachment mechanism. The attachment of the first regions 84 to the front panel 12 can be by an ultrasonic bond, by an adhesive, by glue, by a mechanical fastener such as thread or by other attachment means known by one skilled in the art, etc. Each of the second regions 86 extend forward over a portion of the respective perforation lines 72 and 74 and is removeably attached to the front panel 12. By "removeably attached" is meant that the second regions 86 can be fastened, unfastened and then refastened to the front panel 12 more than once.

Desirably, the pair of attachment members 80 and 82 will cover from between about 25% to about 90% of each of the pair of perforation lines 72 and 74. More desirably, the pair of attachment members 80 and 82 will cover from between about 30% to about 85% of each of the pair of perforation lines 72 and 74. Most desirably, the pair of attachment members 80 and 82 will cover from between about 35% to about 80% of each of the pair of perforation lines 72 and 74. This amount of coverage is important for it is desired that a portion of the pair of perforation lines 72 and 74 be visually present to the user both before and during use of the disposable garment 10. In FIG. 1, one will notice that the shape and location of the perforation lines 72 and 74 make them visible in the front panel 12 above, in the middle, as well as below the attachment members 80 and 82. The greater the amount of visibility of the perforation lines 72 and 74 in the front panel 12, the better.

When the pant-like disposable garment 10 is an incontinent undergarment designed to be worn by older adults who may suffer from poor eye sight, dementia or possibly arthritis, it is best to make them consciously aware of the presence and location of the pair of perforation lines 72 and 74. This will aid them in being able to tear the perforation lines 72 and 74. Also, when the user knows that the attachment members 80 and 82 can be released and reapplied both before as well as after the perforation lines 72 and 74 are broken, it enables the user to keep their disposable garment 10 snug about their waist at all times.

Returning to FIG. 1, the second regions 86 of each of the pair of attachment members 80 and 82 can be formed from a material or contain a piece of material that has hook-like properties. VELCRO® is one such material that can engage into the fibers forming the outer cover 48. In this example, the outer cover 48 would be considered to be a loop material. VELCRO® is a registered trademark of Velcro USA, Inc. having an office at 406 Brown Avenue, Manchester, N.H. 03103. The second regions 86 of the pair of attachment members 80 and 82 is depicted as having two tabs 88 and 90. It should be noted that a single larger tab can be used if desired. However, it has been found that when the front panel 12 has a length dimension or rise (measured parallel to the longitudinal axis Y—Y) that is greater than about six inches (about 15.24 cm), that the two individual tabs 88 and 90 work better than a single larger tab. One reason for this is that the individual tabs 88 an 90 allow for different sections of the front panel 12 to be adjusted independent of the remaining sections. This ability to localize the area of adjustment creates a better fit of the garment 10 to the torso of the user. For example, one can snug up the front panel 12 relative to one or both of the leg opening 68 and 70 without disturbing the fit around the waist opening 66. In addition, the non-parallel arrangement of the pair of perforation lines 72 and 74 relative to the seams 62 and 64, especially when the perforation lines 72 and 74 have a non-linear configuration, seems to fit the curvature of the torso better and thereby provides improved fit of the disposable garment 10.

The pair of perforation lines 72 and 74 and the pair of attachment members 80 and 82 cooperate to allow the waist opening 66 to be opened and closed at least once and desirably more than once. When the perforation lines 72 and 74 are connected and when each of the attachment members, 80 and 82 respectively, bridge across one of the perforation lines 72 and 74, the garment 10 has a closed waist opening 66 and the user can pull the disposable garment 10 up over his or her thighs and around his or her torso. The second region 86 of each of the attachment members 80 and 82 can then be released and refastened to snuggly position the disposable garment 10 onto the wearer's body. During use, if the user needs to go to the bathroom to change the disposable garment 10 or merely wants to check on the condition of the interior of the garment 10, the second region 86 of each of the attachment members 80 and 82 can be released and the pair of perforation lines 72 and 74 can be broken or torn open. This action will allow the front panel 12 to be separated from the remaining portion of the chassis 60. Alternatively, the user can simply inspect the interior of the garment 10 and then refasten the garment 10 by folding the front panel 12 upward around the torso. The second regions 86 of each of the attachment members 80 and 82 are then secured to the front panel 12. The user could also replace the disposable garment 10 without having to completely remove the rest of his or her clothes, for example, his or her pants or slacks. This ability to open and close the disposable garment 10 can occur more than once.

Referring now to FIG. 7, an alternative pant-like disposable garment 10' is shown wherein the first regions 84 of each of the pair of attachment members 80 and 82 is secured to the back panel 22 instead of to the front panel 12. In this embodiment, the second regions 86 of each of the attachment members 80 and 82 extend forward over one of the seams, 62 or 64 respectively, and over a portion of one of the perforation lines, 72 and 74 respectively. The second regions 86 are still removeably attached to the front panel 12 as was explained above. Another difference between the disposable garment 10 and the disposable garment 10' is that the disposable garment 10' has a distance $d_3$ that is greater than a distance $d_4$. $d_3$ is the distance between the perforation lines 72 and 74, approximate the first end 14, while $d_4$ is the distance between the perforation lines 72 and 74 at a point situated between the waist opening 66 and the respective leg openings 68 and 70. Still another difference is that each of the pair of perforation lines 72 and 74 has a concave configuration relative to one of the adjacent seams, 62 and 64 respectively. The concave configuration can be used in the embodiment shown in FIG. 1 as well. The concave configuration may allow for a large portion of the perforation lines 72 and 74 to be visible to the wearer of the disposable garment 10' even when the second regions 86 of the attachment members 80 and 82 are removeably secured to the front panel 12. Any desired configuration for the perforation lines 72 and 74 can be used when the attachment members are secured to the back panel.

Figure 8:
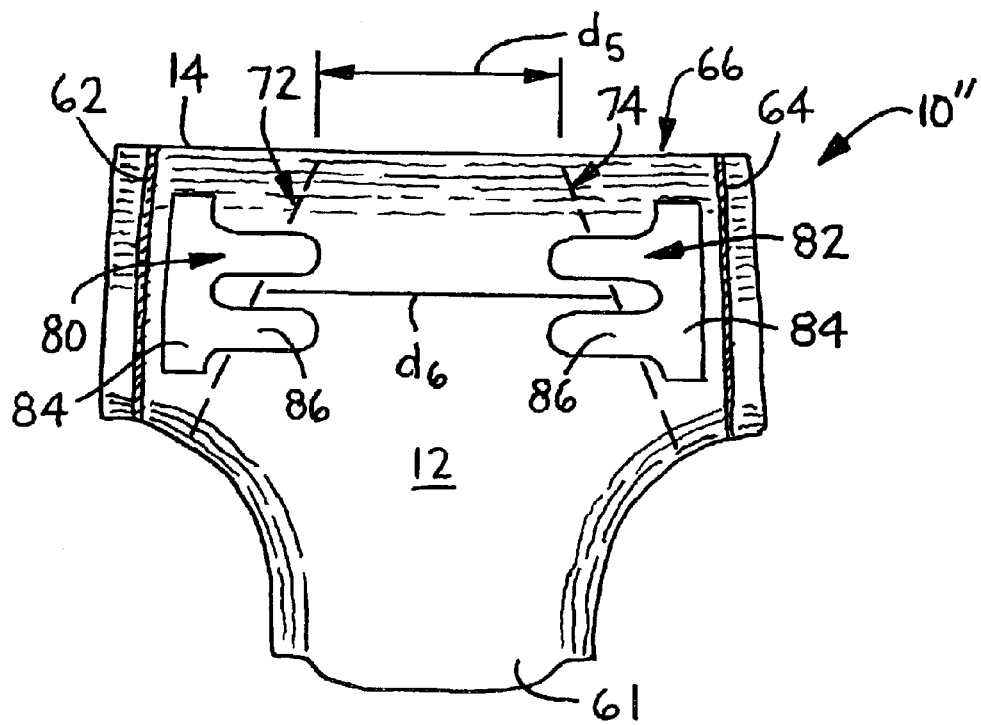
FIG. 8 is a plane view of a portion of a pant-like disposable garment showing a pair of linear perforation lines aligned at an angle so as to be non-parallel to the side seams such that at least about 25% of the perforation lines are visible even when the attachment members are removably fastened over the perforation lines.

Lastly, referring to FIG. 8, a third embodiment is depicted wherein each of the pair of perforation lines 72 and 74 are linear in configuration but each is aligned at an acute angle relative to one of the seams, 62 and 64 respectively. The pair of perforation lines 72 and 74 angle downward from the waist opening 66 toward the seams 62 and 64 such that they approach the seams 62 and 64 adjacent to the leg openings 68 and 70. In this configuration, a distance ($d_5$) located adjacent to the waist opening 66 and between the perforation lines 72 and 74 is less than a distance ($d_6$) located at a point situated between the waist opening 66 and the respective leg opening 68 and 70. It should be noted that the pair of perforation lines 72 and 74 could also be angled downward from the waist opening 66 and outward away from the seams 62 and 64 such that they move farther away from the seams 62 and 64 as they approach the leg openings 68 and 70. The feature of forming the pair of perforation lines 72 and 74 non-parallel to the seams 62 and 64 increases there ability to be visible when the attachment members 80 and 82 are in a closed configuration.

While the invention has been described in conjunction with several specific embodiments, it is evident that many alternatives, modifications and variations will be apparent to those skilled in the art in light of the aforegoing description. Accordingly, this invention is intended to include all such alternatives, modifications and variations that fall within the spirit and scope of the appended claims.

We claim:

1. A pant-like disposable garment for absorbing human discharge comprising:
   a) a front panel;
   b) a back panel;
   c) an absorbent assembly including a liquid pervious bodyside liner, a liquid-impervious outer cover, and an absorbent positioned therebetween, said absorbent assembly further including a pair of end edges, said absorbent assembly being secured to said front panel approximate one of said pair of end edges and being secured to said back panel approximate said other one of said pair of end edges, said front and back panels being joined together by a pair of seams to form a waist opening and a pair of leg openings;
   d) a pair of perforation lines formed in said front panel with each being aligned non-parallel to one of said seams, each of said pair of perforation lines extending from said waist opening to one of said respective leg openings; and
   e) a pair of attachment members each having a first region and a second region, each of said first regions being secured to one side of each of said perforation lines and each of said second regions extending forward over a portion of said respective perforation line and being removeably attached to said front panel, said pair of perforation lines and said pair of attachment members functioning to allow said waist opening to be opened and closed at least once.

2. The pant-like disposable garment of claim 1 wherein each of said pair of perforation lines is tearable and each has a non-linear configuration.

3. The pant-like disposable garment of claim 2 wherein each of said pair of perforation lines has a curved configuration.

4. The pant-like disposable garment of claim 2 wherein each of said pair of perforation lines has a sinusoidal configuration.

5. The pant-like disposable garment of claim 1 wherein each of said pair of perforation lines is aligned at an angle to said respective seam.

6. The pant-like disposable garment of claim 1 wherein said first region of each of said pair of attachment members is secured to said front panel.

7. The pant-like disposable garment of claim 1 wherein said first region of each of said pair of attachment members is secured to said back panel and said second region of each of said attachment members extends forward over a respective seam and a portion of said respective perforation line and is removeably attached to said front panel.

8. The pant-like disposable garment of claim 1 wherein each of said pair of attachment members covers from about 25% to about 90% of said respective perforation line.

9. The pant-like disposable garment of claim 1 wherein said pair of perforation lines is separated by a distance which is less adjacent to said waist opening than at a point located between said waist opening and said pair of leg openings.

10. A pant-like disposable garment for absorbing human discharge comprising:
    a) a front panel;
    b) a back panel;
    c) an absorbent assembly including a liquid pervious bodyside liner, a liquid-impervious outer cover, and an absorbent positioned therebetween, said absorbent assembly further including a pair of end edges, said absorbent assembly being secured to said front panel approximate one of said pair of end edges and being secured to said back panel approximate said other one of said pair of end edges, said front and back panels being joined together by a pair of seams to form a waist opening and a pair of leg openings;
    d) a pair of perforation lines formed in said front panel with each having a non-linear configuration, each of said pair of perforation lines extending from said waist opening to one of said respective leg openings; and
    e) a pair of attachment members each having a first region and a second region, each of said first regions being secured to one side of each of said perforation lines and each of said second regions extending forward over a portion of said respective perforation line and being removeably attached to said front panel, said pair of perforation lines and said pair of attachment members functioning to allow said waist opening to be opened and closed at least once.

11. The pant-like disposable garment of claim 10 wherein each of said pair of perforation lines is tearable and each has an arcuate configuration.

12. The pant-like disposable garment of claim 10 wherein at least about 10% of each of said pair of perforation lines is visible when said second region of each of said pair of attachment members is secured to said front panel.

13. The pant-like disposable garment of claim 10 wherein each of said pair of attachment members covers from between about 30% to about 85% of each of said pair of perforation lines.

14. The pant-like disposable garment of claim 13 wherein each of said pair of attachment members covers from between about 35% to about 80% of each of said pair of perforation lines.

15. The pant-like disposable garment of claim 10 wherein said pair of perforation lines is separated by a distance which is greater adjacent to said waist opening than at a point located between said waist opening and said pair of leg openings.

16. A pant-like disposable garment for absorbing human discharge comprising:
    a) a front panel;
    b) a back panel;
    c) an absorbent assembly including a liquid pervious bodyside liner, a liquid-impervious outer cover, and an absorbent positioned therebetween, said absorbent assembly further including a pair of side edges and a pair of end edges, said absorbent assembly being secured to said front panel approximate one of said pair of end edges and being secured to said back panel approximate said other one of said pair of end edges, said front and back panels being joined together by a pair of seams to form a waist opening and a pair of leg openings, and portions of each of said side edges are aligned adjacent to said respective leg openings and portions of each of said end edges are aligned adjacent to said waist opening;

d) a pair of tearable perforation lines formed in said front panel with each being aligned non-parallel to one of said seams, each of said pair of perforation lines extending from said waist opening to one of said respective leg openings; and e) a pair of attachment members each having a first region and a second region, each of said first regions being permanently secured to one side of each of said pair of perforation lines and each of said second regions extending forward such that each of said pair of attachment members covers from about 25% to about 90% of said respective perforation line and each of said second regions being removeably attached to said front panel, said pair of perforation lines and said pair of attachment members functioning to allow said waist opening to be opened and closed at least once.

17. The pant-like disposable garment of claim 16 wherein each of said pair of perforation lines is aligned at an angle to said respective seam.

18. The pant-like disposable garment of claim 16 wherein each of said pair of perforation lines is non-linear.

19. The pant-like disposable garment of claim 16 wherein each of said pair of perforation lines is formed from a plurality of land and open areas, each of said land and open areas has a length wherein the length of said open areas is at least 3 times greater than the length of said land areas.

20. The pant-like disposable garment of claim 16 wherein said pair of perforation lines is separated by a distance which is less adjacent to said waist opening than at a point located between said waist opening and said pair of leg openings.

* * * * *